United States Patent
Aho et al.

(10) Patent No.: US 10,052,416 B2
(45) Date of Patent: Aug. 21, 2018

(54) ENTEROCUTANEOUS FISTULA TREATMENT

(71) Applicant: Mayo Foundation for Medical Education and Research, Rochester, MN (US)

(72) Inventors: Johnathon M. Aho, Rochester, MN (US); Terry P. Nickerson, Rochester, MN (US); Blake A. Spindler, Rochester, MN (US); Raaj K. Ruparel, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 119 days.

(21) Appl. No.: 15/109,934

(22) PCT Filed: Jan. 7, 2015

(86) PCT No.: PCT/US2015/010408
§ 371 (c)(1),
(2) Date: Jul. 6, 2016

(87) PCT Pub. No.: WO2015/105824
PCT Pub. Date: Jul. 16, 2015

(65) Prior Publication Data
US 2016/0325027 A1 Nov. 10, 2016

Related U.S. Application Data

(60) Provisional application No. 61/924,332, filed on Jan. 7, 2014.

(51) Int. Cl.
*A61M 1/00* (2006.01)
*A61J 15/00* (2006.01)
*A61M 3/02* (2006.01)

(52) U.S. Cl.
CPC ........ *A61M 1/0088* (2013.01); *A61J 15/0015* (2013.01); *A61M 1/0084* (2013.01); *A61M 3/0283* (2013.01); *A61M 2210/106* (2013.01)

(58) Field of Classification Search
CPC .......... A61B 17/00234; A61B 17/0057; A61B 17/12022; A61B 17/12113;
(Continued)

(56) References Cited

U.S. PATENT DOCUMENTS 4,573,965 A * 3/1986 Russo .................. A61M 27/00
604/128
5,645,081 A * 7/1997 Argenta .............. A61M 1/0088
128/897

(Continued)

FOREIGN PATENT DOCUMENTS

WO    WO2013181686 B2    12/2013

OTHER PUBLICATIONS

Kaushal et al., "Management of enterocutaneous fistulas," Clin Colon Rectal Surg., 17(2):79-88, May 2004.
(Continued)

*Primary Examiner* — Nathan R Price
*Assistant Examiner* — Gerald Landry, II
(74) *Attorney, Agent, or Firm* — Fish & Richardson P.C.

(57) ABSTRACT

This document provides devices, systems, and methods for treating patients with wounds that include a fistula. For example, this document provides a multi-lumen tubular device that can deliver wound irrigation, wound suction, and fistuloclysis nutritional support through the lumens of the tubular device.

19 Claims, 3 Drawing Sheets

(58) Field of Classification Search
CPC . A61B 2017/00575; A61F 2013/00536; A61F 13/00068; A61F 2013/0054; A61F 2013/00412; A61M 1/0088; A61M 1/0096; A61M 27/00; A61M 1/0031; A61M 1/0084; A61M 1/0058
USPC .... 604/19, 35, 43, 48, 93.01, 290, 305, 313, 604/317, 319, 541, 543
See application file for complete search history.

(56) References Cited

U.S. PATENT DOCUMENTS

| | | | | |
|---|---|---|---|---|
| 7,837,673 | B2* | 11/2010 | Vogel | A61F 13/0216 |
| | | | | 604/323 |
| 7,931,912 | B2 | 4/2011 | Kanie | |
| 7,981,098 | B2* | 7/2011 | Boehringer | A61M 1/0011 |
| | | | | 604/304 |
| 8,128,655 | B2 | 3/2012 | Wittmann | |
| 8,162,909 | B2 | 4/2012 | Blott | |
| 8,317,774 | B2* | 11/2012 | Adahan | A61M 1/0088 |
| | | | | 604/313 |
| 9,272,080 | B2* | 3/2016 | Weston | A61M 1/0088 |
| 9,808,561 | B2* | 11/2017 | Adie | A61M 1/0088 |
| 2003/0225393 | A1* | 12/2003 | McMichael | A61J 15/0023 |
| | | | | 604/513 |
| 2008/0188820 | A1* | 8/2008 | Joshi | A61M 1/0066 |
| | | | | 604/304 |
| 2008/0281350 | A1* | 11/2008 | Sepetka | A61B 17/0057 |
| | | | | 606/200 |
| 2009/0124988 | A1* | 5/2009 | Coulthard | A61M 1/0088 |
| | | | | 604/313 |
| 2009/0137973 | A1* | 5/2009 | Karpowicz | A61M 1/0001 |
| | | | | 604/313 |
| 2014/0163490 | A1* | 6/2014 | Locke | A61M 1/0031 |
| | | | | 604/319 |
| 2014/0236109 | A1* | 8/2014 | Greener | A61M 1/0088 |
| | | | | 604/319 |
| 2015/0216733 | A1* | 8/2015 | Allen | A61F 13/0206 |
| | | | | 604/319 |
| 2015/0258259 | A1* | 9/2015 | Johannison | A61M 1/0088 |
| | | | | 604/319 |
| 2015/0314112 | A1* | 11/2015 | Griffith | A61M 27/00 |
| | | | | 604/540 |
| 2016/0030722 | A1* | 2/2016 | Anderson | A61F 13/0216 |
| | | | | 604/20 |

OTHER PUBLICATIONS

KCI Licensing, Inc., "V.A.C. Ulta Negative Pressure Wound Therapy System: Monograph," 36 pages, 2012.
International Search Report and Written Opinion for PCT/US2015/010408, dated May 1, 2015, 10 pages.
International Preliminary Report on Patentability for PCT/US2015/010408, dated Jul. 21, 2016, 6 pages.

* cited by examiner

ENTEROCUTANEOUS FISTULA TREATMENT

CROSS REFERENCE TO RELATED APPLICATIONS

This application is a National Stage application under 35 U.S.C. § 371 of International Application No. PCT/US2015/010408, having an International Filing Date of Jan. 7, 2015, which claims the benefit of U.S. Provisional Application No. 61/924,332, filed Jan. 7, 2014. The disclosure of the prior application is considered part of and is incorporated by reference in the disclosure of this application.

BACKGROUND

1. Technical Field

This document relates to devices, systems, and methods for treating patients with wounds that include a fistula. For example, this document relates to a multi-lumen tubular device that can deliver wound irrigation, wound suction, and fistuloclysis nutritional support through the lumens of the tubular device.

2. Background Information

Unresolved healing is a significant issue in medicine. Failure to heal can lead to ulcers (wounds open to the environment) and abscesses. A fistula is a type of abscess cavity characterized by a tunnel running between two hollow organs, or between a hollow organ and the surface of the skin. Inflammatory bowel diseases, such as Crohn's disease, can substantially contribute to the formation of fistulae involving the digestive tract.

Enterocutaneous fistula remain a significant cause of morbidity in the surgical population. They are very difficult to manage as the wounds are continuously contaminated by succus entericus. Current wound management with wet to dry dressings, vacuum devices, and stoma appliances has been unable to effectively reduce the contamination. As such, patients are often hospitalized for prolonged periods of time for repeated dressing chances and significant resources required to manage these wounds. Patients must go prolonged periods of time with no oral intake and are often managed with parenteral nutrition. The need for constant dressing changes, sometimes upwards of six times per day to minimize contamination, as well as the need for parenteral nutrition result in prohibitively high health care costs and resource utilization.

SUMMARY

This document provides devices, systems, and methods for treating patients with wounds that include a fistula. For example, this document provides a multi-lumen tubular device that can deliver wound irrigation, wound suction, and fistuloclysis nutritional support through the lumens of the tubular device.

In general, one aspect of this document features a device for treating a patient with a wound that includes a fistula. In some embodiments, the device comprises an elongate flexible tube and a cup. The cup is attached, or attachable, to the flexible tube. In some embodiments, the elongate flexible tube defines at least three lumens. The elongate flexible tube defines a first lumen that is configured to provide suction to the wound. The elongate flexible tube defines a second lumen that is configured to deliver irrigation fluid to the wound. The elongate flexible tube also defines a third lumen that is configured to extend through the fistula and into an intestine of the patient, such that the patient can receive an infusion of nutritional fluid through the third lumen. In some embodiments, the cup includes (i) a first surface, (ii) a second surface, and (iii) a periphery. In particular embodiments, at least a portion of the second surface has a concavity. The periphery can be sealable to skin surrounding the wound such that the second surface faces the wound, and such that irrigation fluid delivered to the wound through the second lumen is contained between the cup and the skin.

In some implementations, the elongate flexible tube has a proximal end portion and a distal end portion. The flexible tube may be attached to the cup such that the proximal end portion of the flexible tube extends proximally from the first surface and the distal end portion of the flexible tube extends distally from the second surface, when the device is being used to treat the patient. The third lumen may extend farther distally than the first lumen and the second lumen. In some embodiments, the first lumen extends farther distally than the second lumen. The flexible tube optionally defines a plurality of fenestrations that are confluent with the first lumen. The plurality of fenestrations may be located distally of the cup.

In another aspect, this document features a system for treating a patient with a wound that includes a fistula. In some embodiments, the system comprises an elongate flexible tube, a cup attached to the flexible tube, and a suction source or a tube feeding machine (or both). In some embodiments, the elongate flexible tube defines at least three lumens. The elongate flexible tube defines a first lumen that is configured to provide suction to the wound. The elongate flexible tube defines a second lumen that is configured to deliver irrigation fluid to the wound. The elongate flexible tube also defines a third lumen that is configured to extend through the fistula and into an intestine of the patient, such that the patient can receive an infusion of nutritional fluid through the third lumen. In some embodiments, the cup includes (i) a first surface, (ii) a second surface, and (iii) a periphery. In particular embodiments, at least a portion of the second surface has a concavity. The periphery can be sealable to skin surrounding the wound such that the second surface faces the wound and such that irrigation fluid delivered to the wound through the second lumen is contained between the cup and the skin. The suction source can be in fluid communication with the first lumen. The tube feeding machine can be configured to deliver the infusion of nutritional fluid through the third lumen.

In another aspect, this document features a method for treating a patient with a wound that includes a fistula. In some embodiments, the method comprises attaching a multi-lumen tubular device to the patient. The tubular device comprises an elongate flexible tube and a cup that is attached or attachable to the flexible tube. The flexible tube defines a first lumen that is configured to provide suction to the wound. The flexible tube defines a second lumen that is configured to deliver irrigation fluid to the wound. The flexible tube defines a third lumen that is configured deliver an infusion of nutritional fluid to the patient. The cup including (i) a first surface, (ii) a second surface, and (iii) a periphery, at least a portion of the second surface having a concavity. In some embodiments, the attaching comprises inserting a portion of the third lumen through the fistula and into an intestine of the patient, and sealing the periphery to skin surrounding the wound such that the second surface faces the wound and such that irrigation fluid delivered to the wound through the second lumen is contained within a space between the cup and the skin.

In particular implementations, the method further comprises injecting nutritional fluid into and through the third lumen such that the nutritional fluid exits the flexible tube at a location within the intestine of the patient. The method may also comprise injecting irrigation fluid into and through the second lumen such that the irrigation fluid exits the flexible tube and contacts the wound. The method may also comprise applying suction through the first lumen such that the suction is communicated from the first lumen to the space between the cup and the skin.

Particular embodiments of the subject matter described in this document can be implemented to realize one or more of the following advantages. In some embodiments, treatment of patients that have wounds including a fistula can be enhanced using a single device that can provide enteral tube feeding, wound irrigation, and wound suction. The use of such a device and treatment technique may reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides devices, systems, and methods for treating patients with wounds that include, but are not limited to, a fistula, abscesses, ulcers, boils, and the like. For example, this document provides a multi-lumen tubular device that can deliver wound irrigation, wound suction, and fistuloclysis nutritional support through the lumens of the tubular device.

Figure 1:
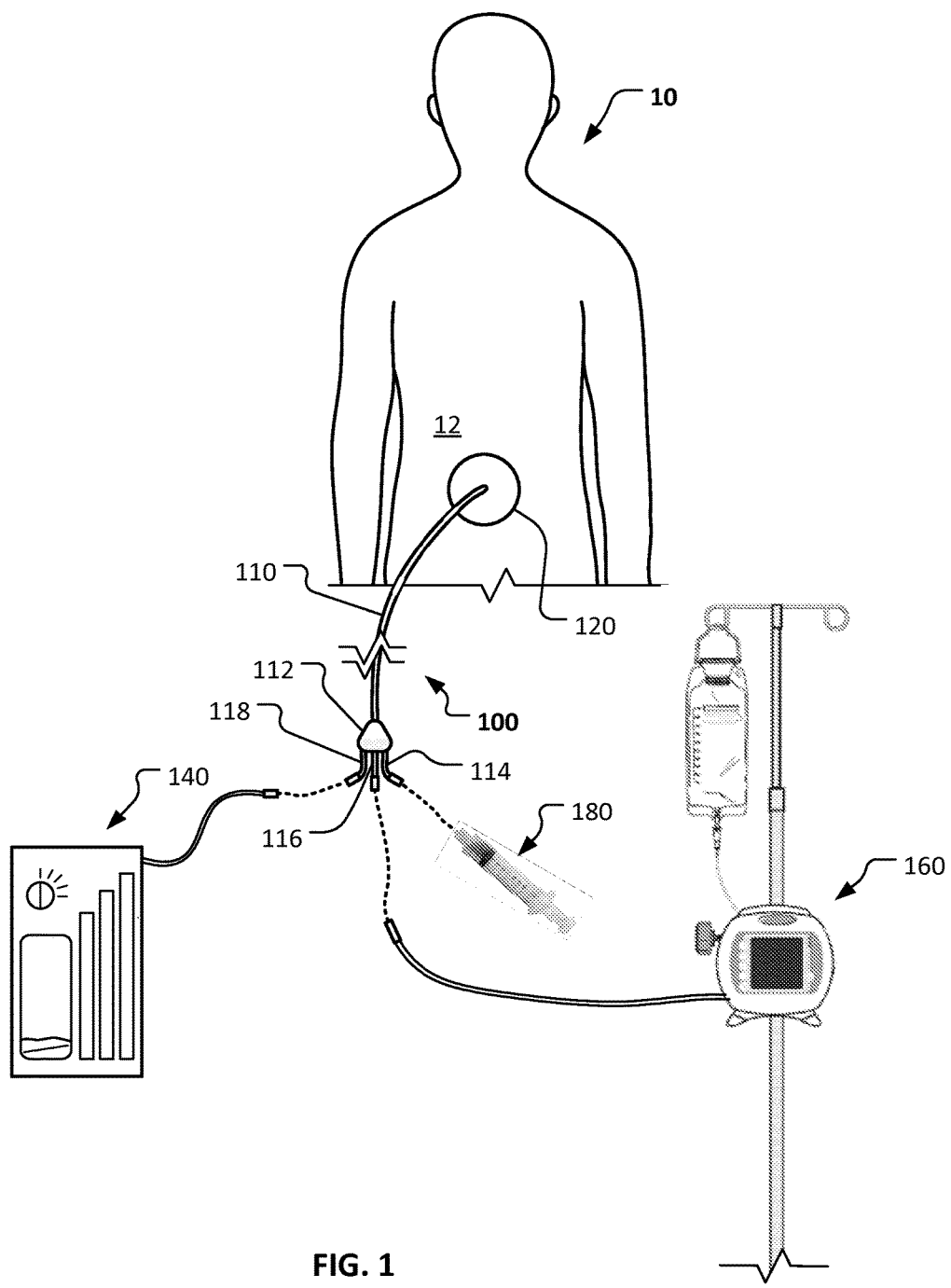
FIG. 1 is a schematic diagram of patient undergoing treatment for a wound that includes a fistula. The treatment is taking place using a multi-lumen tubular device in accordance with some embodiments provided herein.

In reference to FIG. 1, a patient 10 with a wound that includes a fistula (e.g., an enterocutaneous fistula) can be treated using a multi-lumen tubular device 100. Multi-lumen tubular device 100 can optionally be releasably coupled to a suction source 140, a tube feeding machine 160, and an irrigation source 180 as desired in accordance with a clinician's treatment plan for patient 10. While a fistula is used in this example, it should be understood that various other types of wounds (e.g., abscesses, ulcers, boils, trauma, and the like) can be treated using multi-lumen tubular device 100.

As will be described further below, in some embodiments multi-lumen tubular device 100 includes an elongate flexible tube 110 that defines at least three lumens, and a hub 112 that trifurcates the lumens. Hub 112 facilitates the connection of other devices to the at least three lumens individually. In particular embodiments, the at least three lumens includes a first lumen 118 that can convey a negative air pressure (vacuum) for wound suction, a second lumen 114 that can convey an irrigation fluid to the wound, and a third lumen 116 that can convey a nutritional fluid to patient 10. These three lumens may also be referred to herein as suction lumen 118, irrigation lumen 114, and feeding lumen 116 respectively.

In this example system configuration, a suction source 140 is depicted as a separate bedside type of device. In addition, it should be understood that suction source 140 can be integrated with, for example, tube feeding machine 160, or may be a connection to a central source of suction such as a hospital wall vacuum source. Tube feeding machine 160 can also be integrated with other devices in some embodiments, such as suction source 140 and/or irrigation source 180. While irrigation source 180 is depicted as a basic syringe in this example system configuration, irrigation source 180 can be configured differently in some embodiments, including as an automated device that may be integrated with other devices or as a stand-alone device.

Multi-lumen tubular device 100 also includes a cup 120. In use, cup 120 is attached to tube 110. In some embodiments, cup 120 is fixedly attached to tube 110 prior to installation of multi-lumen tubular device 100 to patient 10. In some embodiments, tube 110 is installed to patient 10 first, and then cup 120 is subsequently installed and fixedly attached to tube 110.

In some embodiments, cup 120 is made of a flexible biocompatible polymeric material such as, but not limited to, silicone, PEBAX, PTFE, polyurethanes, and the like, and combinations thereof. In particular embodiments, a reinforcing member, such as nitinol wire(s), is included with the polymeric material to add rigidity to cup 120.

The periphery of cup 120 surrounds the wound being treated. In the depicted embodiment, the periphery of cup 120 is circular. However, other shapes can be used for the periphery of cup 120, such as, but not limited to, square, rectangular, ovular, polygonal, and the like. In some implementations, the periphery of cup 120 may be cut by a clinician to suit the particular topography at the site of installation on patient 10.

The periphery of cup 120 is sealed to skin 12 (and/or other types of tissue around the wound) of patient 10. In some implementations, a medical adhesive is used to seal cup 120 to skin 12. For example, in particular implementations a TEGADERM® film adhesive can be used to seal cup 120 to skin 12. Using such a seal, the wound is segregated by cup 120 from other portions of skin 12 to protect the other portions of skin 12 from contamination and irritation from succus entericus from the fistula. In addition, the seal allows for effective wound irrigation and suction by multi-lumen tubular device 100.

Figure 2:
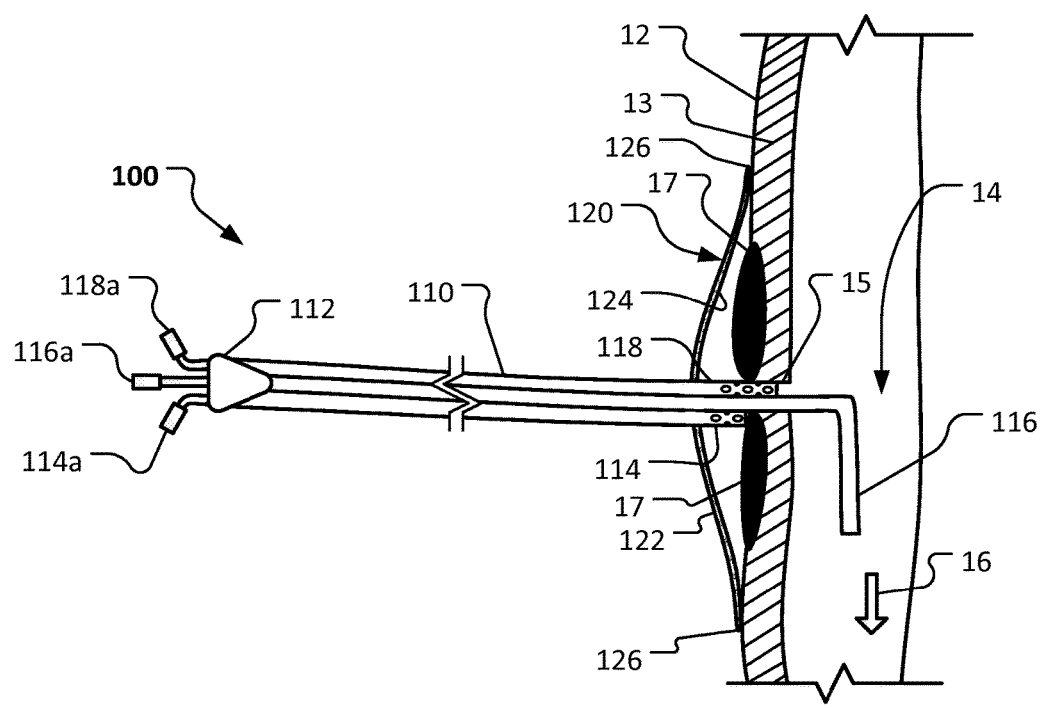
FIG. 2 is a cross-sectional side view of a portion of the patient of FIG. 1 in accordance with some embodiments provided herein.

In reference to FIG. 2, a portion of patient 10 is shown in cross-section. The depicted portion of patient 10 includes skin 12, a subcutaneous fat layer 13, an intestine 14, a fistula 15, and a wound 17. In this example, fistula 15 extends from skin 12 to intestine 14. The direction of flow through intestine 14 is indicated by an arrow 16.

Multi-lumen tubular device 100 is shown installed in patient 10. As described above, multi-lumen tubular device 100 includes, at least, suction lumen 118, irrigation lumen 114, and feeding lumen 116.

In this embodiment, the feeding lumen 116 extends through fistula 15 and terminates within intestine 14. In some implementations, the distal-most tip of feeding lumen 116 is positioned within intestine 14 at a position that is distally located (in reference to the direction of flow 16 through intestine 14) from fistula 15. Feeding lumen 116 can thereby facilitate fistuloclysis nutritional support to patient 10.

Suction lumen 118 can extend partially within fistula 15 in some implementations, but such placement is not required in all implementations. Irrigation lumen 114 can terminate outside of fistula 15 near the wound in some implementations. Suction lumen 118 and irrigation lumen 114 can include one or more fenestrations in some embodiments, and such fenestrations can be confluent with lumens 118 and 114.

While in the depicted embodiment, tube 110 is depicted as a combination of three lumens 114, 116, and 118 that are adjacent and parallel to each other, it should be understood that other configurations of lumens 114, 116, and 118 are envisioned within the scope of this disclosure. For example, in some embodiments at least portions of two or more of lumens 114, 116, and 118 may be coaxial with each other. The at least three lumens 114, 116, and 118 can optionally include fittings 114a, 116a, and 118a respectively, for connection to other devices (e.g., refer to FIG. 1).

A proximal portion of tube 110 extends from cup 120 to fittings 114a, 116a, and 118a. A distal portion of tube 110 extends from cup 120 to the distal terminations of lumens 114, 116, and 118. In some embodiments, other fittings and/or connectors can be included along tube 110.

Multi-lumen tubular device 100 includes cup 120 (shown in cross-section). Cup 120 includes a first surface 122, a second surface 124, and a periphery 126. Second surface 124 can face skin 12 of patient 10. Periphery 126 can be sealed to skin 12 as described above. In some embodiments, second surface 124 includes a concavity. In some embodiments, a space exists between cup 120 and skin 12. The space can be used to facilitate irrigation and suction from irrigation lumen 114 and suction lumen 118 respectively.

Various types of fluid can be supplied to wound 17 of patient 10 via irrigation lumen 114. Such fluids can include, but are not limited to, topical cleansing solutions and suspensions (e.g., saline solution, etc.), antimicrobial and antiseptic solutions, and various other types of therapeutic solutions. In some implementations, the fluid is slowly introduced into the area of wound 17, and is allowed to remain for a period of time before being removed via suction lumen 118. Such introduction and removal of the fluid can be automated or manually performed. In some implementations, the fluid is allowed to dwell (soak) in the area of wound 17 so as to loosen soluble contaminants in wound 17, followed by subsequent removal via suction lumen 118.

In some implementations, a series of different fluids are delivered to wound 17 via irrigation lumen 114. The sealed periphery 126 contains such fluids within the region defined by cup 120, prior to removal via suction lumen 118.

Figure 3:
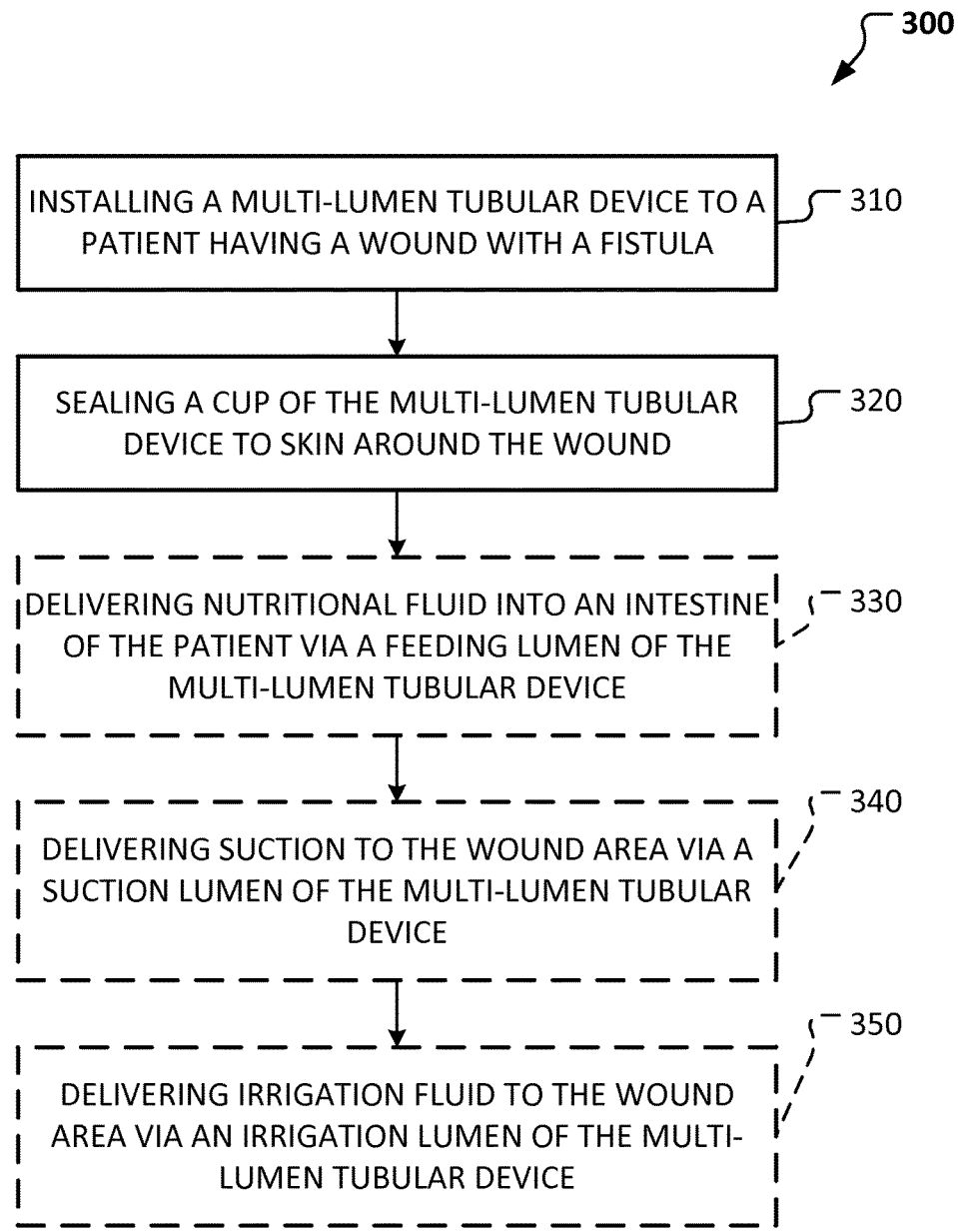
FIG. 3 is flowchart of a method for treating a patient with a wound that includes a fistula in accordance with some embodiments provided herein.

In reference to FIG. 3, a method 300 is provided for treating a patient with a wound that includes a fistula, in accordance with some embodiments provided herein. Method 300 can include the use of a device such as multi-lumen tubular device 100 described above. In some embodiments, a suction source, a tube feeding machine, and/or an irrigation fluid source, and/or a suction source can also be optionally used in conjunction with method 300.

At operation 310, a multi-lumen tubular device is installed on the patient. In some implementations, the multi-lumen tubular device is installed such that a first lumen of the tubular device extends through the fistula and into an intestine of the patient. A lumen that is installed as such can be used for supplying a nutritional fluid to the patient. In some implementations, the multi-lumen tubular device is installed such that a second lumen extends into at least a portion of the fistula. A lumen that extends into a portion of the fistula may be used, for example, to provide suction to remove contaminants and/or irrigation fluids from the wound area, so as to promote healing of the wound. In some implementations, the multi-lumen tubular device is installed such that a third lumen terminates near the wound, but not in the fistula. The third lumen can be used, for example, to provide suction for removing contaminants and/or irrigation fluids from the wound area.

At operation 320, a cup of the multi-lumen tubular device is installed on the patient. In some implementations, the periphery of the cup is sealed to tissue of the patient using adhesives. The periphery of the cup circumscribes the wound. A concave portion of the cup can face the tissue (e.g., skin and/or other tissue) of the patient to create a space between the cup and the tissue/wound of the patient.

At operation 330, a nutritional fluid can be optionally delivered to the patient through a lumen of the multi-lumen tubular device. In some implementations of method 300, the nutritional fluid can be delivered from a tube feeding machine that is coupled to the multi-lumen tubular device. The nutritional fluid can be delivered via the lumen that extends through the fistula and into an intestine of the patient (thereby feeding the patient using a fistuloclysis technique).

At operation 340, suction to remove contaminants and/or irrigation fluids from the wound area can be optionally delivered to the patient through a lumen of the multi-lumen tubular device. In some implementations of method 300, the suction can be delivered by the lumen of the multi-lumen tubular device that extends into a portion of the fistula.

At operation 350, an irrigation fluid can be optionally delivered to the patient through a lumen of the multi-lumen tubular device. In some implementations of method 300, the irrigation fluid can be delivered from a syringe, or from an automated source of irrigation fluid. In particular implementations, the irrigation fluid can be delivered via the lumen that terminates near the wound, but not in the fistula.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A multi-lumen tubular device for treating a patient with a wound that includes a fistula, the device comprising:
   an elongate flexible tube, the flexible tube defining a first lumen that is configured to provide suction to the wound, the flexible tube defining a second lumen that is configured to deliver irrigation fluid to the wound, and the flexible tube defining a third lumen that is configured to extend through the fistula and into an intestine of the patient such that the patient can receive an infusion of nutritional fluid through the third lumen; and
   a cup attached to the flexible tube, the cup including (i) a first surface, (ii) a second surface, and (iii) a periphery, at least a portion of the second surface having a concavity, the periphery being sealable to tissue surrounding the wound such that the second surface faces the wound and such that irrigation fluid delivered to the wound through the second lumen is contained between the cup and the tissue,
   wherein the elongate flexible tube has a proximal end portion and a distal end portion, and wherein the flexible tube is attached to the cup such that the proximal end portion of the flexible tube extends proximally from the first surface and the distal end portion of the flexible tube extends distally from the second surface when the device is being used to treat the patient, and
   wherein the third lumen extends farther distally than the first lumen and the second lumen.

2. The device of claim 1, wherein the first lumen extends farther distally than the second lumen.

3. A multi-lumen tubular device for treating a patient with a wound that includes a fistula, the device comprising:
   an elongate flexible tube, the flexible tube defining a first lumen that is configured to provide suction to the wound, the flexible tube defining a second lumen that is configured to deliver irrigation fluid to the wound, and the flexible tube defining a third lumen that is configured to extend through the fistula and into an intestine of the patient such that the patient can receive an infusion of nutritional fluid through the third lumen; and
   a cup attached to the flexible tube, the cup including (i) a first surface, (ii) a second surface, and (iii) a periphery, at least a portion of the second surface having a concavity, the periphery being sealable to tissue surrounding the wound such that the second surface faces the wound and such that irrigation fluid delivered to the wound through the second lumen is contained between the cup and the tissue,
   wherein the flexible tube defines a plurality of fenestrations that are confluent with the first lumen, and wherein the plurality of fenestrations are located distally of the cup.

4. The device of claim 3, wherein the elongate flexible tube has a proximal end portion and a distal end portion, and wherein the flexible tube is attached to the cup such that the proximal end portion of the flexible tube extends proximally from the first surface and the distal end portion of the flexible tube extends distally from the second surface when the device is being used to treat the patient.

5. The device of claim 3, wherein at least two of the first lumen, the second lumen, and the third lumen are coaxial with each other.

6. The device of claim 3, further comprising:
   a suction source that is in fluid communication with the first lumen.

7. The system of claim 6, wherein the elongate flexible tube has a proximal end portion and a distal end portion, and wherein the flexible tube is attached to the cup such that the proximal end portion of the flexible tube extends proximally from the first surface and the distal end portion of the flexible tube extends distally from the second surface when the device is being used to treat the patient.

8. The device of claim 3, further comprising:
   a tube feeding machine that is configured to deliver the infusion of nutritional fluid through the third lumen.

9. The system of claim 8, wherein the elongate flexible tube has a proximal end portion and a distal end portion, and wherein the flexible tube is attached to the cup such that the proximal end portion of the flexible tube extends proximally from the first surface and the distal end portion of the flexible tube extends distally from the second surface when the device is being used to treat the patient.

10. A method for treating a patient with a wound that includes a fistula, the method comprising:
    attaching a multi-lumen tubular device to the patient, the tubular device comprising:
      an elongate flexible tube, the flexible tube defining a first lumen that is configured to provide suction to the wound, the flexible tube defining a second lumen that is configured to deliver irrigation fluid to the wound, and the flexible tube defining a third lumen that is configured deliver an infusion of nutritional fluid to the patient; and
      a cup attached to the flexible tube, the cup including (i) a first surface, (ii) a second surface, and (iii) a periphery, at least a portion of the second surface having a concavity,
    wherein the attaching comprises inserting a portion of the third lumen through the fistula and into an intestine of the patient, and wherein the attaching comprises sealing the periphery to skin surrounding the wound such that the second surface faces the wound and such that irrigation fluid delivered to the wound through the second lumen is contained within a space between the cup and the skin; and
    injecting nutritional fluid into and through the third lumen such that the nutritional fluid exits the flexible tube at a location within the intestine of the patient.

11. The method of claim 10, further comprising injecting irrigation fluid into and through the second lumen such that the irrigation fluid exits the flexible tube and contacts the wound.

12. The method of claim 10, further comprising applying suction through the first lumen such that the suction is communicated from the first lumen to the space between the cup and the skin.

13. A method for treating a patient with a wound that includes a fistula, the method comprising:
   attaching a multi-lumen tubular device to the patient, the tubular device comprising:
      an elongate flexible tube, the flexible tube defining a first lumen that is configured to provide suction to the wound, the flexible tube defining a second lumen that is configured to deliver irrigation fluid to the wound, and the flexible tube defining a third lumen that is configured deliver an infusion of nutritional fluid to the patient; and
      a cup attached to the flexible tube, the cup including (i) a first surface, (ii) a second surface, and (iii) a periphery, at least a portion of the second surface having a concavity,
   wherein the attaching comprises inserting a portion of the third lumen through the fistula and into an intestine of the patient, and wherein the attaching comprises sealing the periphery to skin surrounding the wound such that the second surface faces the wound and such that irrigation fluid delivered to the wound through the second lumen is contained within a space between the cup and the skin;
   injecting nutritional fluid into and through the third lumen such that the nutritional fluid exits the flexible tube at a location within the intestine of the patient;
   injecting irrigation fluid into and through the second lumen such that the irrigation fluid exits the flexible tube and contacts the wound; and
   applying suction through the first lumen such that the suction is communicated from the first lumen to the space between the cup and the skin.

14. The device of claim 3, wherein the first lumen extends farther distally than the second lumen.

15. The device of claim 1, wherein at least two of the first lumen, the second lumen, and the third lumen are coaxial with each other.

16. The device of claim 1, wherein the flexible tube defines a plurality of fenestrations that are confluent with the first lumen, and wherein the plurality of fenestrations are located distally of the cup.

17. The device of claim 3, wherein the third lumen extends farther distally than the first lumen and the second lumen.

18. The device of claim 1, further comprising:
   a suction source that is in fluid communication with the first lumen.

19. The device of claim 1, further comprising:
   a tube feeding machine that is configured to deliver the infusion of nutritional fluid through the third lumen.

* * * * *